(12) United States Patent
Tokumoto et al.

(10) Patent No.: US 8,771,781 B2
(45) Date of Patent: Jul. 8, 2014

(54) METHOD OF COATING MICRONEEDLE

(75) Inventors: Seiji Tokumoto, Tsukuba (JP);
Toshiyuki Matsudo, Tsukuba (JP);
Tetsuji Kuwahara, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1195 days.

(21) Appl. No.: 12/599,394

(22) PCT Filed: Oct. 18, 2007

(86) PCT No.: PCT/JP2007/070377
§ 371 (c)(1),
(2), (4) Date: Nov. 9, 2009

(87) PCT Pub. No.: WO2008/139648
PCT Pub. Date: Nov. 20, 2008

(65) Prior Publication Data
US 2010/0280457 A1    Nov. 4, 2010

(30) Foreign Application Priority Data

May 15, 2007    (JP) .................................. 2007-129736

(51) Int. Cl.
*A61M 3/00*    (2006.01)
*B05D 1/18*    (2006.01)

(52) U.S. Cl.
USPC .......... 427/2.1; 427/2.28; 427/2.3; 427/430.1; 604/46

(58) Field of Classification Search
None
See application file for complete search history.

(56) References Cited

U.S. PATENT DOCUMENTS

| 6,855,372 B2 * | 2/2005 | Trautman et al. ............. 427/287 |
| 2002/0128599 A1 | 9/2002 | Cormier et al. |
| 2005/0123550 A1 * | 6/2005 | Laurent et al. ............. 424/184.1 |
| 2010/0280457 A1 | 11/2010 | Tokumoto et al. |

FOREIGN PATENT DOCUMENTS

| JP | 11286439 A | 10/1999 |
| JP | 2001506904 A | 5/2001 |
| JP | 2004504120 A | 2/2004 |
| JP | 2004520152 A | 7/2004 |
| JP | 2005-74139 A | 3/2005 |
| JP | 2007-75352 A | 3/2007 |
| WO | 9828037 A1 | 7/1998 |
| WO | 0207813 A1 | 1/2002 |

(Continued)

OTHER PUBLICATIONS

Gill et al. "Coated microneedles for transdermal delivery" Journal of Controlled Release 117 ( Oct. 24, 2006). pp. 227-237.*

(Continued)

*Primary Examiner* — Cachet Sellman
(74) *Attorney, Agent, or Firm* — Sughrue Mion, PLLC

(57) ABSTRACT

The present invention provides a method of coating microneedles by which the microneedles mounted on a microneedle device are coated accurately and easily in a mass-producible manner. In this method, a microneedle device (22) with a plurality of microneedles (21) is mounted on a table (23), while a mask plate (25) with a plurality of apertures (24) is fixed to a frame member (26), and a coating solution (27) is drawn in the direction of arrow A on the mask plate (25) using a spatula (28) to fill the apertures (24) with the coating solution. The microneedles (21) are inserted in the apertures (24) before or after the filling of the apertures (24) with the coating solution (27) to coat the microneedles (21).

14 Claims, 6 Drawing Sheets

(56) References Cited

FOREIGN PATENT DOCUMENTS

| | | |
|---|---|---|
| WO | 02074173 A1 | 9/2002 |
| WO | 02094368 A1 | 11/2002 |
| WO | 2005/044366 A2 | 5/2005 |
| WO | 2006055799 A1 | 5/2006 |
| WO | 2006138719 A2 | 12/2006 |
| WO | 2008139648 A1 | 11/2008 |

OTHER PUBLICATIONS

The International Searching Authority, "Written Opinion," issued in connection with International Patent Application No. PCT/JP2007/070377, dated Nov. 20, 2007.

The International Bureau of WIPO, "International Preliminary Report on Patentability," issued in connection with International Patent Application No. PCT/JP2007/070377, dated Nov. 24, 2009.

\* cited by examiner

METHOD OF COATING MICRONEEDLE

TECHNICAL FIELD

The present invention relates to a microneedle coating method of coating microneedles of a microneedle device.

BACKGROUND ART

Conventionally, a microneedle device is known as a device for enhancing transdermal drug absorption. The microneedles of a microneedle device aims to puncture the outermost layer of the epidermis, the corneum, and various sizes and shapes are proposed in the hope of a noninvasive administration method (e.g., Patent Document 1).

Similarly, various drug application methods using a microneedle device are proposed. Known examples include that a drug is coated on a microneedle surface; a groove or hollow is provided in a microneedle to allow a drug or a biological component to penetrate therethrough, a microneedle itself is mixed with a drug, etc. (e.g., Patent Document 2).

Thus, as a way of effectively facilitating transdermal drug absorption using a microneedle device, there is a method by which a drug is coated on a part of the surface of a microneedle device. In particular, when a drug is coated on a part of a microneedle device (especially only on microneedles), all or most of an applied drug is delivered into the body and hence such a method is useful as a very efficient and accurate administration method.

Further, since these proposed microneedle devices are all provided with extremely small protrusions having a height of about several tens to several hundreds micrometers, it can be easily assumed that a transdermal drug absorption and efficiency greatly vary depending on drug applications.

Patent Document 3 discloses a microdroplet coating method using the ink jet method, etc., by which droplets are selectively released to only microneedles.

However, the document does not describe a method by which only a part (microneedles) of a microneedle device is coated by precise position control and release control. In the typical ink jet methods, the releasable amount is a picoliter order, thereby limiting an amount coatable at a time. Further, the viscosity of a coating solution is limited to the lower side (<50 cps). For this reason, it is thought to be difficult to selectively coat only microneedles in a highly reproducible manner.

Patent Document 4 discloses a method of selectively coating only the tip of a microneedle with a solution containing a drug. More specifically, the method controls the level of a drug to be coated by immersing a microneedle in the coating solution controlled at a given depth. The depth of a coating solution is controlled using a cylindrical roller and the liquid viscosity of the solution is limited to about 500 cps or lower, thereby achieving a quantitative coating. This method enables the selective coating of a drug only to microneedles and is hence considered useful as a method of coating a drug quantitatively. However, since the viscosity range of a coating solution is limited to a low viscosity range (about 500 cps or lower), a drug amount coated by a single immersion is limited to a certain extent. As a result, when a coated amount must be controlled, particularly when a large amount of drug needs to be coated, the immersion-drying cycle must be inevitably repeated a number of times.

When the operation of shifting a coating solution by rolling using a cylinder is repeated, the concentration of the coating solution is liable to increase gradually. Further, when an attempt is made to coat a drug only on an microneedle by this method, it is quite predictable that the capillary phenomenon occurs depending on the surface tension of a coating solution used, causing the wicking phenomenon wherein the solution extends to the basal surface (root portion) of microneedle or to the bottom of microneedle substrate.

Patent Document 5 discloses a coating method using a removable mask phase. In this method, using phase-separable solvents having different volatilities as masking materials, a physiologically active substance is coated on the tip of a microneedle by volatilizing the solvents step by step. This method enables the drug coating only on a microneedle, but it is expected that the drying step requires some time depending on drugs and the residual mask phase on the microneedle is also concerned.

Patent Document 6 discloses a coating method of coating needles on the microneedle substrate and developed based on the dip coating method. This method employs a mask (physical mask) having apertures formed thereon corresponding to the pitch of microneedles in order to prevent the wicking phenomenon caused by the surface tension of a coating solution from occurring, and controls the coating amount by controlling the surface position of the coating solution and the contact level of microneedles. However, in this method, since the reservoir storing the coating solution is directly connected to the mask apertures in which the microneedles are inserted, the level of coating amount is liable to vary significantly depending on the position of inserting the needles. Even when the insertion level is strictly controlled, it is essential to maintain the balance between the surface tension of coating solution and the surface energy of needles. When this balance is lost, the coating level and amount to the microneedles may change. Further, the coating solution level with respect to the mask surface must be strictly controlled which requires a power unit to always maintain the solution at a constant level.

Patent Document 1: National Publication of International Patent Application No. 2001-506904
Patent Document 2: National Publication of International Patent Application No. 2004-504120
Patent Document 3: National Publication of International Patent Application No. 2004-520152
Patent Document 4: WO02/074173A1
Patent Document 5: WO2006/055799A1
Patent Document 6: WO2006/138719A2

DISCLOSURE OF THE INVENTION

Problems to be Solved by the Invention

The techniques already proposed as described above pose various problems. Consequently, there is a demand for a method of coating a drug in a required amount precisely, easily and in a mass producible manner on a part of a microneedle device (especially to a microneedle and the tip of microneedle), i.e., on an extremely small thin three dimensional structure such as a microneedle. However, when a physiologically active substance (a drug) needed to be coated on a part of a microneedle device (especially to a microneedle and the tip of a microneedle), there has been no method of coating a drug in a required amount on a microneedle precisely, easily and in a mass producible manner.

Consequently, an object of the present invention is to provide a microneedle coating method of coating the microneedles formed on a microneedle device precisely, easily and in a mass producible manner.

Means for Solving the Problems

The present inventors conducted extensive studies to solve the above problems and found a method of coating a microneedle or the tip thereof with a coating solution in a required amount by a single operation by utilizing a screen printer which has never been used in a past for the microneedle coating. The inventors further pursued the studies and ensured the coating quantitativeness, whereby the present invention is accomplished.

The method of coating microneedles of the present invention comprises the steps of filling a coating solution on a mask plate having apertures into the apertures using a filling means, and inserting microneedles of a microneedle device to the apertures filled with the coating solution to coat the microneedles. Further, the method of coating microneedles of the present invention comprises the steps of inserting the microneedles of a microneedle device to the apertures formed on a mask plate, and filling a coating solution on the mask plate into the apertures using a filling means to coat the microneedles. The above filling means may be a spatula.

The coating amount to the microneedle described above can be adjusted by changing at least one of: a. an opening diameter of the apertures formed on the mask plate; b. a viscosity of the coating solution; c. a clearance between the mask plate and the microneedle substrate; d. a spatula pressure; e. a speed of spatula stroke; f. a thickness of the mask plate; and g. an attack angle between the spatula and the mask plate. In the above case, the opening diameter of the apertures formed on the mask plate may be 100 $\mu m^2$ to 90000 $\mu m^2$, which exceeds a cross sectional area of the microneedle at a lower end of the apertures when inserting the microneedle as described above. The viscosity of the coating solution described above may be 500 cps to 60000 cps. The clearance between the mask plate and the microneedle substrate described above may be 0 to 500 µm. The spatula pressure described above may be 0.001 to 0.4 MPa. The speed of spatula stroke described above may be 2 to 800 mm/sec. The thickness of the mask plate described above may be 10 to 500 µm. The attack angle between the above spatula and the mask plate described above may be 65° to 90°.

Further, the steps described above may be carried out at a relative humidity of 70.0 to 100% RH. The coating solution described above may contain a high molecular carrier compatible with a high molecular physiologically active substance. The term "high molecular physiologically active substance" used herein refers to a physiologically active substance having a molecular weight of 1000 or more. The term "compatible with" used herein is defined as a state wherein a phase separation clearly occurs by centrifugation after adjusting the solution or no coagulation is observed. The high molecular carrier described above may be a polysaccharide. The polysaccharide described above is one or more selected from the group consisting of pullulan, hydroxypropylcellulose and hyaluronic acid. The microneedle device according to the present invention comprises the microneedles coated by the coating method as described hereinbefore.

Effect of the Invention

The present invention can provide a method of coating microneedles by which the microneedles of a microneedle device are coated precisely, easily and in a mass producible manner. Owing to the present invention, the quantitative coating of a physiologically active substance on the microneedles is enabled, and a microneedle device having coated microneedles can also be mass-produced by using a screen printer or basic movement employed by the screen printing. Further, the coating solution can almost homogeneously contain a high molecular physiologically active substance due to the high molecular carrier compatible with the polymeric physiologically active substance contained therein. More specifically, the coagulation and phase separation of a high molecular physiologically active substance caused by the addition of a water soluble polymer can be prevented, resulting in a practically homogeneous solution, whereby the highly precise coating of a high molecular physiologically active substance to the microneedles is enabled. Further, the coating amount of a high molecular physiologically active substance can be regulated by adjusting the viscosity of water soluble polymer. In this manner, the convenience of the microneedle is remarkably enhanced.

Figure 1:
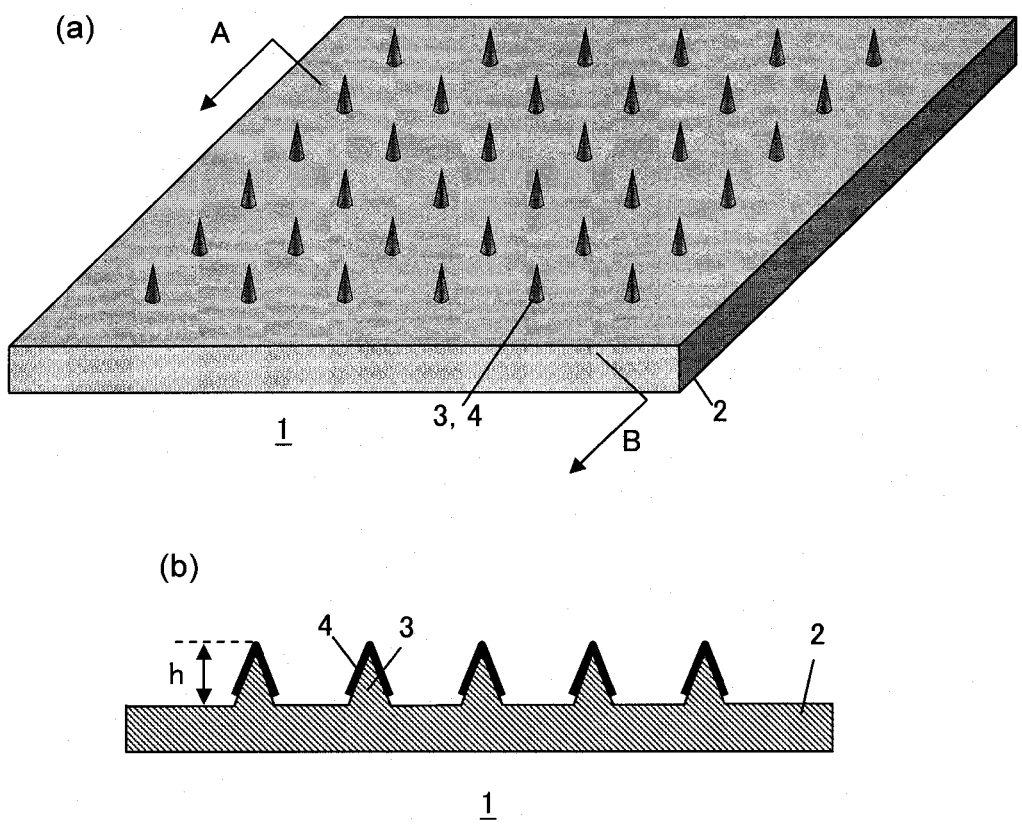
FIG. 1 shows an embodiment of the microneedle device usable in the present invention, wherein (a) is a perspective view and (b) is a sectional view taken along the line A-B of (a)

DESCRIPTION OF SYMBOLS 1, 22 Microneedle devices
2 Microneedle substrate
3, 21 Microneedles
4 Coating
23 Table
24 Apertures
25 Mask plate
26 Frame member
27 Coating solution
28 Spatula

BEST MODE FOR CARRYING OUT THE INVENTION

Examples of the microneedle coating method of the present invention are hereinafter described, however, an embodiment of the microneedle device provided with microneedles usable in the present invention is first described.

FIG. 1 shows an embodiment of the microneedle device usable in the present invention, wherein (a) is a perspective view and (b) is a sectional view taken along the line A-B of (a). As shown in FIG. 1(a), a microneedle device 1 has a microneedle substrate 2 and a plurality of microneedles 3 capable of punching the skin and two-dimensionally disposed on the microneedle substrate 2. The microneedle 3 has a coating 4 applied thereon using a coating carrier as a means of retaining a physiologically active substance.

The microneedle device is not limited to the purpose of administrating a physiologically active substance, but is herein referred to as coating carrier as a means for retaining a physiologically active substance. The coating 4 is preferably in a state which is firmly adhered to the entire or a part of the surface of the microneedle 3.

The microneedle 3 is preferably fabricated using a non-metallic synthetic or natural resin material. The shape of the microneedle 3 is conical in the present examples, but the present invention is not limited thereto, and may be a multi-sided pyramid such as four-sided pyramid, or the like; or even be different shapes.

As described above, the microneedle device comprises microneedles (needles) piercing the skin or mucosa and a microneedle substrate supporting the needles. A plurality of microneedles are arranged on the substrate. The microneedle is a microstructure, and the height (length) h thereof is preferably 50 to 500 µm. The length of microneedle herein is made 50 µm or more to ensure transdermal administration of a physiologically active substance, and 500 µm or less to prevent the microneedle from contacting nerves thereby definitely reducing the possible pains and avoiding the bleeding which could happen otherwise. A length less than 500 µm can also efficiently deliver the amount of physiologically active substance into the skin.

The microneedle used herein is a protrusion structure which, in a broader sense, refers to needle configurations or the structures encompassing needle configurations. When the microneedle has a conical structure, the diameter at the basal surface thereof is typically about 50 to 200 µm. The microneedle is not limited to needle-shaped one having a tapered tip, but includes those having no tapered tip.

The microneedle substrate is a foundation to support the microneedles, and the configuration thereof is not limited. For example, the substrate may be provided with through holes by which a physiologically active substance can be delivered from the back thereof. Examples of the material for microneedle or substrate include silicon, silicon dioxide, ceramic, metals (stainless steel, titanium, nickel, molybdenum, chromium, cobalt, etc.) and synthetic or natural resin materials. However, in consideration of the antigenicity of microneedle and the unit price of materials, particularly preferable materials are biodegradable polymers such as polylactic acid, polyglycolide, polylactic acid-co-polyglycolide, pullulan, capronolactone, polyurethane, polyanhydride, etc., synthetic or natural resin materials such as polycarbonate, polymethacrylic acid, ethylenevinyl acetate, polytetrafluoroethylene, polyoxymethylene, or like non-biodegradable polymers. Further preferable examples include polysaccharides such as hyaluronic acid, pullulan, dextran, dextrin or chondroitin sulfate.

As for the density of microneedle (needles), the needles are typically spaced apart row-wise in a manner so that the density of about 1 to 10 needles per millimeter (mm) is provided. Each row is typically spaced apart in the distance substantially equal to the gap between needles in a row, and the needle density ranges from 100 to 10000 per square centimeter. A needle density of 100 or more can pierce the skin efficiently, whereas a needle density exceeding 10000 makes it difficult to impart to the microneedle the strength capable of piercing the skin.

Examples of the microneedle fabrication method include wet etching process or dry etching process using a silicone substrate, precision machinings using metals or resins (electron discharge method, laser processing, dicing processing, hot embossing, injection molding processing, etc.), machinery cutting, etc. The needle part and the support part are molded to an integrated unit by these processing methods. An example of method of hollowing the needle part include a method in which a secondary processing such as laser processing, etc., is carried out after the fabrication of needle part.

The method of coating microneedles of the present invention is hereinafter described in reference to Examples.

Figure 2:
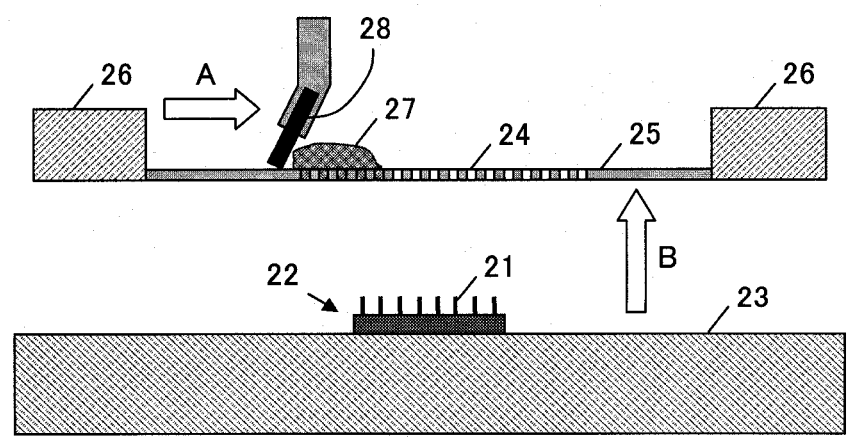
FIG. 2 is a schematic view showing an embodiment of the cross section of printing portion in the screen printer usable in the microneedle coating method of the present invention.

FIG. 2 is a schematic view showing an embodiment of the cross section of printing portion in the screen printer usable in the microneedle coating method of the present invention. In the present examples, a screen printer and a mask plate (screen plate) are used. The screen printer usable is, for example, Newlong screen printer (e.g., LS-150TVA). As shown in the figure, the microneedle device 22 having a plurality of microneedles 21 is mounted on the table 23. Meanwhile, the mask plate 25 having a plurality of apertures 24 is fixed to the frame member 26. The coating solution is filled into the apertures 24 using a filling means. The spatula 28 is used as the filling means in the present examples. More specifically, the coating solution 27 is drawn (swept) by the spatula 28 in the direction of arrow A on the mask plate 25, whereby the coating solution is filled into the apertures 24. The microneedles 21 are inserted into the apertures 24 before or after the coating solution is filled. The spatula 28 used herein includes the scrapers and squeegees used for the screen printing, and the scrapers and squeegees can be used in the present examples. The insertion of the microneedles 21 into the apertures 24 may be achieved by moving the table 23 in the direction of arrow B, or conversely it may be achieved by moving the frame member 26 in the direction opposite to that of arrow B. Alternatively, the table and frame member may be moved at the same time. The microneedles 21 are thus coated. This coating method will be described later.

The coating amount to the microneedle 21 can be adjusted by changing at least one of the opening diameter of aperture in the mask plate, the viscosity of coating solution, the clearance between the mask plate and the microneedle substrate, the spatula pressure, the speed of spatula stroke, the thickness of mask plate, and the attack angle between the spatula and the mask plate.

Figure 3:
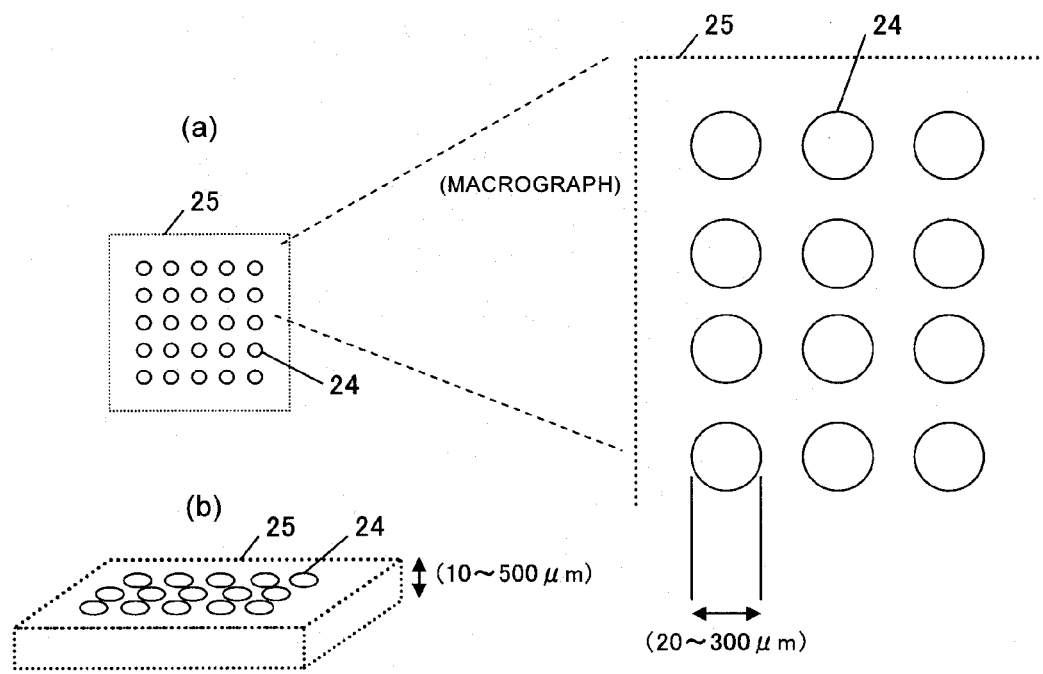
FIG. 3 is a schematic view showing an embodiment of the mask plate shown in FIG. 2, wherein (a) is a plan view and (b) is a perspective view.

FIG. 3 is a schematic view showing an embodiment of the mask plate shown in FIG. 2, wherein (a) is a plan view and (b) is a perspective view. As shown in the figure, the mask plate 25 is provided with a plurality of apertures 24. The mask plate, also called screen plate, comes in a form of mesh structured (mesh) mask woven using a fiber such as silk, nylon, Tetron, or the like, or using a stainless steel wire, or the like, or in a form of metal mask plate processed by cutting out a metal such as stainless steel, etc. It is known that the process precision of these masks affects the precision of printed matters. The metal mask is preferably used to coat the microneedle with a physiologically active substance. The opening diameter and shape of the aperture in the mask plate can be selected according to the needle configuration and pitch of the microneedle. The opening diameter of the aperture in the mask plate may be, for example, 20 to 300 µm. The thickness of mask plate may be, for example, 10 to 500 µm. Those having a thickness of about 50 to 200 µm are typically used, but a mask plate having a thickness of 10 to 50 µm is used for an especially small amount of coating, whereas a mask plate having a thickness of 200 to 500 μm is used for a large amount of coating. The mask aperture 24 may be a through hole or a blind hole. When the aperture is a blind hole, the thickness of mask plate described above means a thickness to the bottom of the aperture 24.

The metal mask plates usable are porous metal sheets such as stainless steel, copper-base alloy, nickel-base alloy, or the like. The specification of the aperture to be formed, the thickness of mask plate and the composition of coating solution are adjusted to fill the apertures in the mask plate with a given amount of the coating solution and only the coating solution filled is transferred to a part (needle part or tip part) of the microneedle, thereby enabling the fabrication of microneedle coated with a drug. Since the number of apertures is determined in accordance with the number of needles of the microneedles, it is not particularly limited but is preferably 100 to 3000 apertures/cm$^2$, and more preferably 400 to 1800 apertures/cm$^2$. The specifications of aperture need to be set so as to give the shape and size required to insert the microneedles to a given level, and the area of a single aperture is preferably 100 to 90000 μm$^2$/aperture, and more preferably 2500 to 50000 μm$^2$/aperture. The amount of coating solution increases as the area of the aperture becomes greater, regardless the configuration thereof. The mask apertures can be selected from either through holes or blind holes depending on the insertion depth of microneedles. When the mask apertures are through holes, the microneedles can be inserted to the apertures from either side of the mask plate, whereas when the mask apertures are blind holes, the microneedles are inserted from the side of mask plate on which the apertures are formed. Accordingly, the spatula position can be selected from either the upper side or bottom side insofar as the side of mask plate has the apertures formed thereon.

In the screen printing, the special spatulas called scrapers or squeegees as described above may be used for filling a coating solution to the apertures formed on the mask. The scraper is mainly used in the purpose of returning a coating solution swept to one side by a squeegee back to the original position while performing the filling operation. The squeegee serves to fill a coating solution and is also capable of transferring the coating solution onto a subject. The squeegee is commonly available in the configurations such as flat type, four-sided diamond cut type, diamond cut type, cylindrical type, etc. The materials include synthetic rubber, silicone rubber, metals, plastic, ceramic, etc., with urethane rubber squeegee being the most preferable. Also available is a hermetic squeegee for storing a coating solution in a hermetic head. The filling amount of coating solution is adjustable by controlling the pressure of scraper or squeegee (spatula), the squeegee speed or scraper speed (speed of spatula stroke), or the attack angle (a placement angle of a scraper or squeegee (spatula) to the mask plate), or two or more of these conditions. The spatula pressure is typically 0.001 to 0.4 MPa, and preferably 0.01 to 0.2 MPa. The speed of spatula stroke is preferably 2 to 800 mm/sec. The attack angle of the spatula against the mask plate is preferably 65° to 90°.

The coating amount and thickness to the microneedle can be freely increased or decreased by controlling the specifications of mask plate or the physical properties (polymer type, concentration) of coating solution, and also adjustable by controlling the filling amount in the mask apertures achieved by the changes of the clearance between the mask plate and microneedle as a subject to be printed, printing pressure, squeegee speed (or scraper speed), attack angle or mask thickness.

The coating solution is transferred to the microneedle either at the same time of squeegeeing across the mask plate (filling the coating solution) or after filling a given amount of the coating solution to the mask plate, and the transfer timing can be selected according to the physical properties of coating solution and the configuration of microneedle. These two methods are described hereinafter in detail, however, in either methods it is preferred that the filling amount to the apertures formed on the mask plate be constant at all times.

Figure 4:
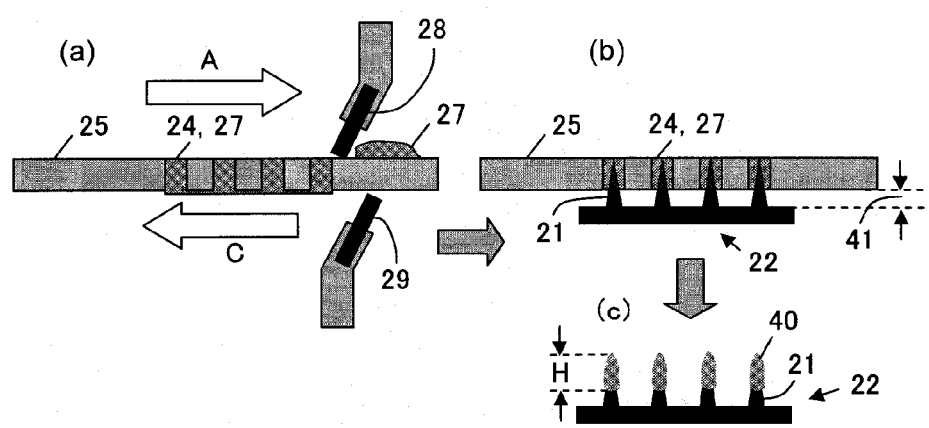
FIG. 4(a) to (c) are diagrams showing an embodiment of the coating method by which microneedles are inserted into apertures after a coating solution is filled into the mask apertures.

FIG. 4(a) to (c) are diagrams showing an embodiment of the coating method wherein the microneedles are inserted in the apertures after filling the coating solution in the mask apertures. In this method, as shown in FIG. 4(a), the coating solution 27 is first swept across the mask plate 25 using the spatula 28 in the direction of arrow A and filled into the apertures 24. When the filled coating solution 27 is squeezed out of the apertures 24 during this operation, the coating solution squeezed out is removed as necessary by sweeping with the spatula 29 in the direction of arrow C on the underside of mask plate 25. Subsequently, as shown in FIG. 4(b), the microneedles 21 are inserted in the apertures 24 formed on the mask plate 25. Thereafter, as shown in FIG. 4(c), the microneedles 21 are pulled out of the apertures 24 formed on the mask plate 25. Thus, the coating 40 of the coating solution 27 is applied to the microneedles 21.

The coating height (H) of the microneedles 21 is adjusted by the clearance (gap) 41 shown in FIG. 4(b). The clearance 41 is defined as the distance from the basal surface of microneedle to the mask surface (excluding the substrate thickness), and is determined in accordance with the tension of mask and the length of microneedle. The distance of clearance 41 preferably ranges from 0 to 500 μm. When the distance of the clearance 41 is 0, the microneedles 21 are entirely coated.

Figure 5:
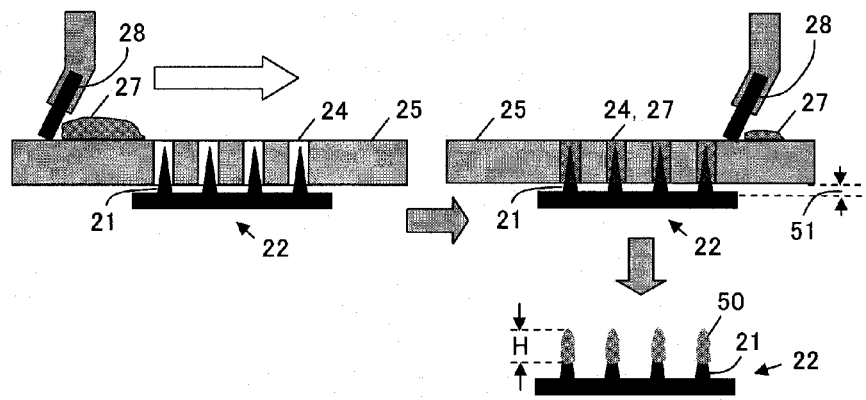
FIG. 5(a) to (c) are diagrams showing an embodiment of the method of coating microneedles by which a coating solution is filled into the mask apertures after the microneedles are inserted into the mask apertures.

FIG. 5(a) to (c) are diagrams showing an embodiment of the microneedle coating method wherein the coating solution is filled into the mask apertures after the microneedles are inserted in the mask apertures. In this method, as shown in FIG. 5(a), the microneedles 21 are first inserted in the apertures 24 formed on the mask plate 25. Subsequently, the coating solution 27 is swept across the mask plate 25 using the spatula 28 in the direction of arrow A, and filled into the apertures 24 as shown in FIG. 5(b). The coating solution 27 filled coats the part of microneedles that is inserted into the apertures 24. Thereafter, the microneedles 21 are pulled out of the apertures 24 formed on the mask plate 25 as shown in FIG. 5(c). Thus, the coating 50 of the coating solution 27 is applied to the microneedles 21.

The coating height (H) of the microneedles 21 is adjusted by the clearance (gap) 51 shown in FIG. 5(b). The clearance 51 is defined as the distance from the basal surface of microneedle to the mask surface (excluding the substrate thickness), and is determined in accordance with the tension of mask and the length of microneedle. The distance of clearance 51 preferably ranges from 0 to 500 μm. When the distance of the clearance 51 is 0, the microneedles 21 are entirely coated.

To minimize the changes of drug concentration and physical properties caused by the solvent volatilization of coating solution occurred at the time of filling and transferring to the mask plate, it is preferable that the installation environment of the device, i.e., the temperature and humidity around the table, mask plate and subject to be printed be controlled invariably. To prevent the solvent from transpiring, it is preferable to either decrease the temperature or increase the humidity or to control the both of them. When the temperature is not controlled, the humidity at room temperature is a relative humidity of 50 to 100% RH, and preferably 70.0 to 100% RH. When the humidity is less than 50% RH, the solvent is significantly volatilized, causing the physical properties of coating solution to change. The humidification method is not limited insofar as the intended humidity condition is attained, and examples include gas system, steam vaporizer system, water spray system, etc. For the thickener to be mixed in the coating solution, it is preferable to select an aqueous solution polymer having a high wettability and moisture retention to best control the solvent volatilization.

Figure 7:
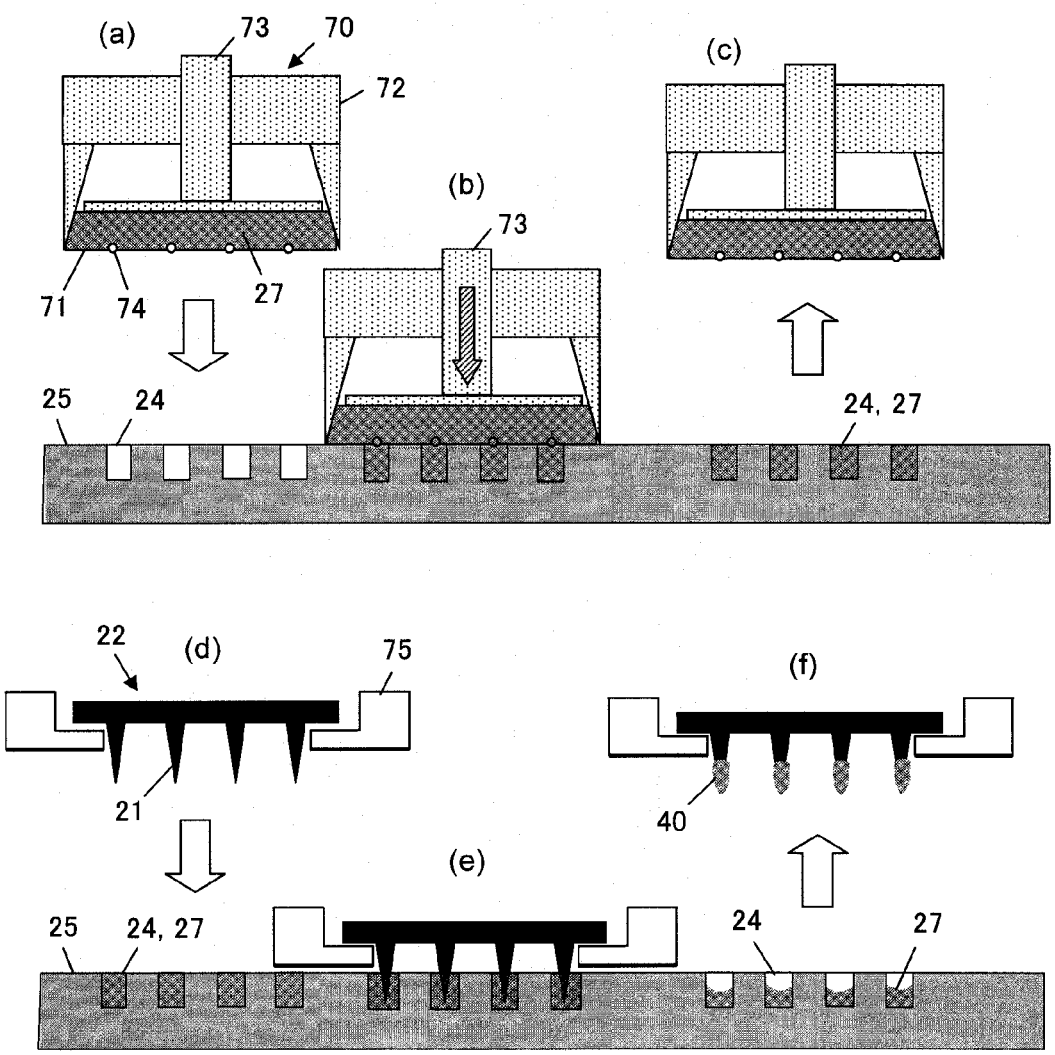
FIG. 7(a) to (f) are diagrams showing other embodiments of microneedle coating methods.
Figure 8:
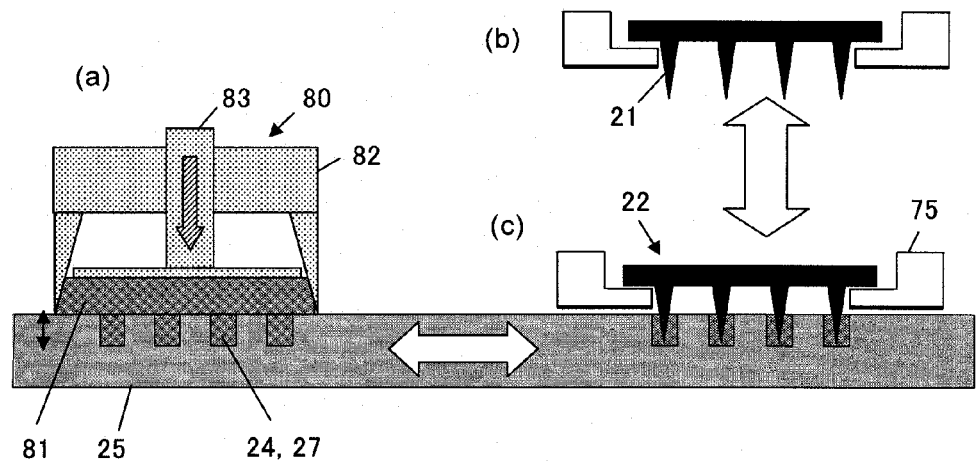
FIG. 8(a) to (c) are diagrams showing another embodiment of microneedle coating method.

There is another embodiment of the coating method as shown in FIG. 7 to minimize the changes of drug concentration and physical properties caused by the solvent volatilization of the coating solution. The coating solution supplier 70 is used in this method. The coating solution supplier 70 is provided with an air tight coating solution container 71, a supporting member 72 supporting the air tight container 71, and a pressing rod 73 pressing the air tight container 71. The air tight container 71 has a plurality of coating solution inlets 74, from which the coating solution 27 is delivered when pressed down by the pressing rod 73. The inlets 74 may be provided with, for example, a valve gear to maintain the air tightness of the air tight container 71. As shown in FIG. 7(a), the coating solution supplier 70 is brought into intimate contact with the apertures 24 formed on the mask plate 25. Subsequently, the air tight container 71 is pressed down the direction of the arrow illustrated using the pressing rod 73 as shown in FIG. 7(b). Thus, the coating solution 27 is filled into the apertures 24. After filling, the coating solution supplier 70 is moved away upward as shown in FIG. 7(c), and continuously the mask plate 25 and/or microneedle device 22 is moved so that the apertures 24 in which the coating solution 27 is filled and the microneedles 21 of the microneedle device 22 held by the holding members 75 settle in the corresponding position to each other as shown in FIG. 7(d). Thereafter, the microneedles 21 are inserted in the apertures 24 as shown in FIG. 7(e). After inserting the microneedles 21, the microneedles 21 are coated with the coating 40 when pulled out of the apertures as shown in FIG. 7(f). Alternatively, the coating method shown in FIG. 8(a) to (c) can also be employed. In this method, the coating solution 27 is held in the hermetic spatula structure 81 supposed by the supporting member 82 of the coating solution supplier 80 and filled into the apertures 24 of the mask plate 25 by pressing using the pressing rod 83. Subsequently, the mask plate 25 is moved to immediately under the microneedles 21 of the microneedle 22 held by the holding members 75, and the microneedles 21 are inserted in the apertures 24. The mask plate 25 may be moved immediately under the microneedles 21 by either moving the mask plate 25 or the hermetic spatula structure 81. The microneedles 21 are inserted in the apertures 24 and then pulled out therefrom, whereby the coating is applied to the microneedles 21.

The coating solution can coat the microneedle with a physiologically active substance by incorporating therein purified water and/or high molecular coating carrier or purified water and/or low molecular coating carrier. Examples of the high molecular coating carrier include polyethylene oxide, polyhydroxymethylcellulose, hydroxypropylcellulose, polyhydroxypropylmethylcellulose, polymethylcellulose, dextran, polyethylene glycol, polyvinyl alcohol, pullulan, hyaluronic acid, etc., and examples of the low molecular coating carrier include salts such as sodium chloride and saccharides such as glucose. The coating solution containing these coating carriers is coated on a part, the whole or the tip of the microneedles and then dried.

The coating carrier is preferably a high molecular coating carrier, but not particularly limited thereto. Preferable examples among them include water soluble polymers having a hydroxy group such as polyethylene oxide, polyhydroxymethylcellulose, hydroxypropylcellulose, polyhydroxypropylmethylcellulose, polymethylcellulose, dextran, polyethylene glycol, polyvinyl alcohol, pullulan, hyaluronic acid, etc. More preferable among these are polysaccharides such as polyhydroxymethylcellulose, hydroxypropylcellulose, polyhydroxypropylmethylcellulose, polymethylcellulose, dextran, pullulan, hyaluronic acid, etc.

The content of the coating carrier in the coating solution is 1 to 70% by weight, preferably 1 to 40% by weight, and particularly preferably 3 to 25% by weight. The coating carrier sometimes needs to have a moderate viscosity to prevent the running, and is required to have a viscosity of about 100 to 100000 cps. The viscosity is more preferably 500 to 60000 cps, and more preferably 500 to 50000 cps. When the viscosity is within this range, the intended amount of coating solution can be applied at single operation without depending on the material of microneedle. Generally, the higher the viscosity is, the greater the amount of coating solution tends to be.

The coating thickness of microneedle is below 50 µm, preferably 25 µm, and more preferably 1 to 10 µm. The coating thickness is typically an average thickness measured across the microneedle surface after dried. The coating thickness can be typically increased by applying a plurality of coating carrier films, that is, by repeating the coating step after the coating carrier is firmly adhered.

The height (length) h of microneedle is preferably 50 to 500 µm as described above. The coating height (H) of microneedle varies depending on the height h of microneedle, but can range from 0 to 500 µm, typically from 10 to 500 µm, and preferably from 30 to 300 µm. The range is determined in accordance with the amount of physiologically active substance to be administered, and the height is adjustable by controlling the mask plate thickness, squeegee pressure (impression), clearance, etc. The coating solution coated is firmly adhered by drying after application.

The liquid composition used for coating the microneedle is prepared by mixing a biocompatible carrier and an efficacious active substance to be delivered, and, optionally, mixing either one of the coating adjuvants with a volatile liquid. The volatile liquid may be water, dimethyl sulfoxide, dimethylformamide, ethanol, isopropyl alcohol or a mixture thereof. Water is most preferable among these. The liquid coating solution or suspension can contain an efficacious physiologically active substance in a concentration of typically 0.1 to 65% by weight, preferably 1 to 30% by weight, and more preferably 3 to 20% by weight. The coating is preferably in a firmly adhered state. The term "firmly adhered state" used herein refers to a state wherein the coating carrier is almost uniformly adhered to a subject. Immediately after the coating application, the coating carrier is firmly adhered in a dried state achieved by air drying, vacuum drying, freeze drying or a combination thereof, however, after transdermal administration, it may not always be firmly adhered in a dried state since the carrier may retain a moisture content or an organic solvent in equilibrium with an ambient atmosphere.

Other known formulation adjuvants may be added to the coating unless they adversely affect the properties such as the solubility and viscosity required for coating and the characteristics and physical properties of dried coated film.

The physiologically active substance (drug) used in the present invention is usually a high molecular compound, but is not limited thereto. The high molecule refers to a molecular weight of 1000 or more as a criterion, but the upper limit of the molecular weight is not limited. The high molecular compounds are peptide, protein, DNA, RNA, and the like, but are not limited thereto. Examples include α-interferon β-interferon for multiple sclerosis, erithropoietin, follicle-stimulating hormone (FSH), follitropin β, follitropin α, G-CSF, GM-CSF, human villosity adenotropic hormone, leutinizing hormone, calcitonin salmon, glucagon, GNRH antagonist, insulin, human growth hormone, filgrastim, heparin, low molecular weight heparin, parathyroid hormone (PTH), somatropin, etc. Examples of vaccines include influenza vaccine, Japanese encephalitis vaccine, *rotavirus* vaccine, Alzheimer disease vaccine, arteriosclerosis vaccine, cancer vaccine, nicotine vaccine, diphtheria vaccine, tetanus vaccine, *pertussis* vaccine, Lyme disease vaccine, rabies vaccine, *diplococcus-pneumoniae* vaccine, yellow fever vaccine, cholera vaccine, vaccinia vaccine, *tuberculosis* vaccine, rubella vaccine, measles virus vaccine, mumps vaccine, and *botulinum* vaccine, herpesvirus vaccine, other DNA vaccines, hepatitis B virus vaccine, etc.

However, the molecular weight is not limited, and examples of low molecular compound include hypnogenesis/tranquilizers (flurazepam hydrochloride, rilmazafone hydrochloride, phenobarbital, amobarbital, etc.); antipyretic/anti-inflammatory agents (butorphanol tartrate, perisoxal citrate, acetaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, etc.); steroidal anti-inflammatory agents (hydrocortisone, prednisolone, dexamethasone, betamethasone, etc.); analeptic/psycho-stimulants (methamphetamine hydrochloride, methylphenidate hydrochloride, etc.); tranquilizers (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazodone, lofepramine, milnacipran, duloxetine, venlafaxine, chlorpromazine hydrochloride, thioridazine, diazepam, meprobamate, etizolam, etc.); hormone drugs (estradiol, estriol, progesterone, norethisterone acetate, metelonone acetate, testosterone, etc.); local anesthetic (lidocaine hydrochloride, procaine hydrochloride, tetracaine hydrochloride, dibucaine hydrochloride, propitocaine hydrochloride, etc.); urinary drugs (oxybutynin hydrochloride, tamsulosin hydrochloride, propiverine hydrochloride, etc.); skeletal muscle relaxants (tizanidine hydrochloride, eperisone hydrochloride, pridinol mesilate, suxamethonium chloride, etc.); genital drugs (ritodrine hydrochloride, meluadrine tartrate); anti-epileptic drugs (sodium valproate, clonazepam, carbamazepine, etc.); autonomic agents (carpronium chloride, neostigmine bromide, bethanechol chloride, etc.); anti-Parkinson's disease agents (pergolide mesilate, bromocriptine mesilae, trihexyphenidyl hydrochloride, amantadine hydrochloride, ropinirole hydrochloride, talipexole hydrochloride, cabergoline, droxidopa, piperiden, selegiline hydrochloride, etc.); diuretics (hydroflumethiazide, furosemide, etc.); respiratory accelerators (loberine hydrochloride, dimorpholamine, naloxone hydrochloride, etc.); anti-migraine agents (dihydroergotamine mesilate, sumatriptan, ergotamine tartrate, flunarizine hydrochloride, cyproheptadine hydrochloride, etc.); antihistamines (clemastine fumarate, diphenhydramine tannate, chlorpheniramine maleate, diphenylphraline hydrochloride, promethazine, etc.); bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, etc.); cardiotonic (isoprenaline hydrochloride, dopamine hydrochloride, etc.); coronary vasodilators (diltiazem hydrochloride, verapamil hydrachloride, isosorbide dinitrate, glycerol trinitrate, nicorandil, etc.); telangiectasis agents (nicametate citrate, tolazoline hydrochloride, etc.); non-smoking adjuvants (nicotine, etc.); circulatory system agents (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride, etc.); arrhythmic agents (propranolol hydrochloride, alprenolol hydrochloride, procainamide hydrochloride, mexiletine hydrochloride, nadolol, disopyramide, etc.); anti-malignant ulcer agents (cyclophosphamide, fluorouracil, tegaful, procarbazine hydrochloride, ranimustine, irinotecan hydrochloride, fluridine, etc.); anti-lipaemia agents (pravastatin, simvastatin, bezafibrate, probucol, etc.); blood sugar depressant (glibenclamide, chlorpropamide, tolbutamide, glymidine sodium, glybuzole, buformin hydrochloride); antiulcer drug (proglumide, cetraxate hydrochloride, spizofurone, cimetidine, glycopyrronium bromide); choleretic drugs (ursodesoxycholic acid, osalmid, etc.); gastrointestinal motility enhancer (domperidone, cisapride, etc.); heaptic disease agents (tiopronin etc.); anti-allergic agents (ketotifen fumarate, azelastine hydrochloride, etc.); antivirotics (aciclovir etc.); anti-vertigo agents (betahistine mesilate, difenidol hydrochloride, etc.); antibiotic (cefaloridine, cefdinir, cefpodoxime proxetil, cefaclor, clarithromycin, erythromycin, methylerythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, etc.); anti-addiction agents (cyanamide etc.); anorectic agents (mazindol etc.); chemotherapic drugs (isoniazid, ethionamide, pyrazinamide, etc.); blood coagulation promoter (ticlopidine hydrochloride, warfarin potassium); anti-Alzheimer agents (physostigmine, donepezil hydrochloride, tacrin, arecoline, xanomeline, etc.); serotonin receptor antagonist antiemetics (ondansetron hydrochloride, granisetron hydrochloride, ramosetron hydrochloride, azasetron hydrochloride, etc.); gout suppressants (colchicine, probenecid, sulfinpyrazone, etc.); narcotic painkillers (fentanyl citrate, morphine sulfate, morphine hydrochloride, codein phosphate, cocaine hydrochloride, pethidine hydrochloride, etc.) As long as a molecular weight is about 1000, physiologically active substances such as vaccines, low molecular peptides, saccharides, nucleic acids, etc., may also be used.

These drugs are used singly or two or more may be used in combination. If a salt is pharmaceutically acceptable, a drug in the form of either inorganic salt or organic salt is, needless to say, encompassed. The drug is basically contained in the coating carrier, but can also be separately supplied later via the through holes (apertures) formed in the substrate of microneedle without being contained in the coating carrier.

EXAMPLES

Example 1

Coating Test Using BSA/Pullulan

A coating solution was prepared using the Japanese Pharmacopoeia pullulan as the coating carrier and 10 to 30% BSA (Bovine serum albumin) as a protein model drug, and applied as a coating to the microneedles. A pullulan concentration in each coating solution was maintained at 20%. The coating method was carried out by the following procedure.
1. A mask plate (metal mask) was mounted on a PET liner (mask specifications: 100 μm thickness, opening aperture diameter 200 μm, 31 lines×31 rows/square (1 cm²).
2. A 100 μl coating solution was dropped on the mask.
3. The coating solution was filled into the apertures formed on the mask by squeegeeing.
4. The microneedles (length 250 μm) were temporarily inserted in the mask apertures so as to give a clearance of 150 μm, and then the microneedles were pulled away from the mask to coat only the tip of microneedles with the drug.

For performing the coating under a high humidity condition, the above procedure was followed in a globe box to carry out the coating operation under the maintained relative humidity condition of 90% or higher. The coating operation was conducted 10 consecutive patches, and the BSA amount coated on each microneedle was measured by a protein assay (BCA method).

Figure 6:
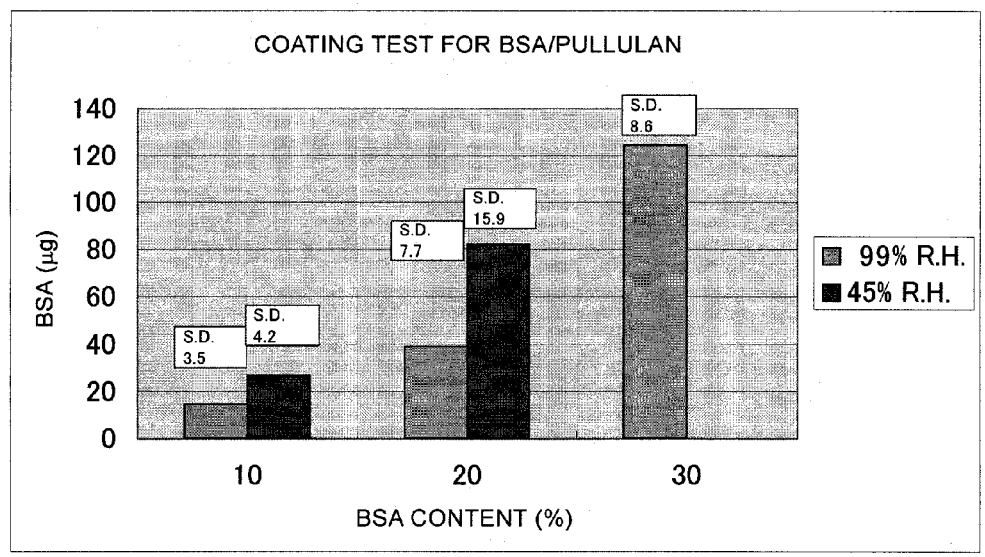
FIG. 6 is a graph showing an example of the coating test using BSA/pullulan.

FIG. 6 is a graph showing an embodiment of the coating test using BSA/pullulan. In the graph, the horizontal axis shows BSA content (%) and the longitudinal axis shows BSA coating amount (μg). This Example shows the results of the BSA coating amount applied by the filling conducted under atmospheres of a relative humidity (RH) of about 45% and about 99%. In the graph, the abbreviation "S.D." stands for a standard deviation. As shown in the graph, the increase in BSA amount which depends on the BSA concentration was confirmed under any humidity conditions. With 30% BSA, 100 μg or more of a drug was able to be coated by a single coating operation. A 20% pullulan solution practically exhibited a viscosity of about 5000 cps (20% aqueous solution), and the viscosity of each solution to which BSA is further added was about 7000 cps with 10% BSA, about 9000 cps with 20%, and about 15000 cps with 30%. The BSA coating amount with the 20% group was about 2.6 times that with the 10% BSA group, and about 8.3 times with the 30% BSA group, showing the tendency of significant increase. These results reveal that the BSA amount coated is greatly affected by not only the drug concentration increase but also a physical property change (viscosity increase) of the coating solution associated with the drug concentration increase. This result verifies that the drug coating amount is controllable by optimizing the drug concentration and the coating carrier concentration.

However, under a relative humidity condition of about 45%, the viscosity of coating solution is found to be liable to increase during the continuous coating operation. In particularly with 30% BSA, the stringiness phenomenon associated with the viscosity increase is observed, failing to carry out the coating of 10 consecutive patches. Since the phenomena are thought to be attributed to the transpiration of moisture in the coating solution, the similar coating operation was carried out under a high humidity condition (about 99%) using a steam vaporizer humidifier. As a result, the coating amount was slightly lower than that of under a humidity condition of about 45%, but the viscosity increase found during the coating operation was not observed at all. The stringiness phenomenon was not observed even with 30% BSA. The comparison in the standard deviation values of each case also shows lower values when the coating was carried out under a high humidity condition, whereby usefulness of the coating under a high humidity condition is indicated. These results reveal that the coating operation under a high humidity atmosphere not only has an effect in maintaining the constant drug concentration of coating solution but also is useful for maintaining the physical properties of coating solution, thereby consequently enhancing the coating precision.

Example 2

Compatibility Verification Test Between Each Polymer and BSA or OVA

Operation Procedure

Each polymer was mixed with BSA or OVA in accordance with the conditions shown in Tables 1 and 2 below to prepare aqueous solutions respectively, which were observed for presence/absence of the coagulation occurrence and the phase separation occurrence after the centrifugal degassing (centrifugation conditions are shown in the table) to evaluate the compatibility (homogeneous liquid=o, inhomogeneous liquid=x). In Tables 1 and 2, o means a polymer having the compatibility and x means a polymer having no compatibility. The symbol % used hereinafter indicates % by weight. The contents in the coating solution were measured by performing the coating by the method shown in FIG. 2 described earlier and the extraction was carried out using 1 mL of purified water to measure a BSA or OVA content (an amount adhered). The term "Not measurable" herein means no polymer adherence to the needle was observed.

TABLE 1

| Polymer | Polymer concentration (%) | OVA concentration (%) | Compatibility (Centrifugation conditions) | Coating content (μg) |
| --- | --- | --- | --- | --- |
| Pullulan | 20 | 20 | ○ (15000 rpm × 2 min) | 50 |
| Pullulan | 15 | 16.7 | ○ (15000 rpm × 2 min) | 16 |
| Pullulan | 7.5 | 16.7 | X | — |
| Pullulan | 5 | 16.7 | X | — |
| Hydroxypropylcellulose-SSL | 15 | 16.7 | X | — |
| Hydroxypropylcellulose-SSL | 20 | 16.7 | X | — |
| Hydroxypropylcellulose-SSL | 25 | 16.7 | X | — |
| Hydroxypropylcellulose-SL | 25 | 25 | ○ (15000 rpm × 2 min) | 41 |
| Hydroxypropylcellulose-SL | 15 | 30 | X | — |
| Hydroxypropylcellulose-L | 13.3 | 16.7 | ○ (3000 rpm × 2 min) | 9 |
| Hydroxypropylcellulose-L | 16.7 | 16.7 | ○ | 16 |
| Hydroxypropylcellulose-L | 20 | 16.7 | X | — |
| Hydroxypropylcellulose-L | 16 | 20 | X | — |
| Hydroxypropylcellulose-L | 13.3 | 20 | X | — |
| Hydroxypropylcellulose-L | 15 | 30 | X | — |
| Hydroxypropylcellulose-H | 4 | 16.7 | X | — |
| Hydroxypropylcellulose-H | 3 | 16.7 | ○ (5000 rpm × 2 min) | 6 |
| Hydroxypropylcellulose-H | 2 | 16.7 | ○ (5000 rpm × 2 min) | 5 |

TABLE 1-continued

| Polymer | Polymer concentration (%) | OVA concentration (%) | Compatibility (Centrifugation conditions) | Coating content (μg) |
|---|---|---|---|---|
| Hydroxypropylcellulose-H | 1.5 | 16.7 | ○ (5000 rpm × 2 min) | — |
| Hydroxypropylcellulose-H | 1 | 16.7 | ○ (5000 rpm × 2 min) | 1 |
| Methylcellulose (SM-25) | 7.5 | 16.7 | X | — |
| Methylcellulose (SM-25) | 4 | 16.7 | X | — |
| Methylcellulose (SM-25) | 2 | 16.7 | X | — |
| Methylcellulose (SM-400) | 5 | 16.7 | X | — |
| Methylcellulose (SM-400) | 3 | 16.7 | ○ (5000 rpm × 2 min) | 7 |
| Methylcellulose (SM-400) | 1 | 16.7 | X | — |
| Methylcellulose (SM-8000) | 2.7 | 16.7 | X | — |
| Methylcellulose (SM-8000) | 4 | 16.7 | X | — |
| Methylcellulose (SM-8000) | 3 | 16.7 | X | — |
| Methylcellulose (SM-8000) | 2 | 16.7 | ○ (15000 rpm × 2 min) | 3 |
| Methylcellulose (SM-8000) | 1 | 16.7 | X | — |
| Hyaluronic acid (MW900000) | 4 | 16.7 | ○ (15000 rpm × 2 min) | 2 |
| Hyaluronic acid (MW900000) | 3 | 16.7 | ○ (15000 rpm × 2 min) | 4 |
| Hyaluronic acid (MW900000) | 2 | 16.7 | ○ (15000 rpm × 2 min) | 4 |
| Hyaluronic acid (MW900000) | 1 | 16.7 | ○ (15000 rpm × 2 min) | 3 |
| Hyaluronic acid (MW2000000) | 2 | 16.7 | X | — |
| Partially neutralized polyacrylate (NP-600) | 3 | 16.7 | ○ (15000 rpm × 2 min) | Not measurable |
| Partially neutralized polyacrylate (NP-600) | 1.5 | 16.7 | ○ (15000 rpm × 2 min) | Not measurable |
| Partially neutralized polyacrylate (NP-800) | 3 | 16.7 | ○ (15000 rpm × 2 min) | Not measurable |
| Partially neutralized polyacrylate (NP-800) | 1.5 | 16.7 | ○ (15000 rpm × 2 min) | Not measurable |
| Polyethylene glycol-20000 | 20 | 16.7 | X | — |
| Polyethylene glycol-20000 | 10 | 16.7 | X | — |
| Polyvinyl alcohol | 10 | 16.7 | X | — |
| Polyvinyl alcohol | 5 | 16.7 | X | — |

TABLE 2

| Polymer | Polymer concentration (%) | BSA concentration (%) | Compatibility | Coating content (μg) |
|---|---|---|---|---|
| Pullulan | 15 | 30 | ○ (15000 rpm × 2 min) | 30 |
| Pullulan | 20 | 20 | ○ (15000 rpm × 2 min) | 18 |
| Hydroxypropylcellulose-SSL | 35 | 16.7 | X | — |
| Hydroxypropylcellulose-SSL | 20 | 16.7 | X | — |
| Hydroxypropylcellulose-SSL | 10 | 16.7 | X | — |
| Hydroxypropylcellulose-SSL | 37.5 | 10 | X | — |
| Hydroxypropylcellulose-SL | 25 | 20 | ○ (15000 rpm × 2 min) | 20 |
| Hydroxypropylcellulose-SL | 20 | 16.7 | X | — |
| Hydroxypropylcellulose-SL | 16.7 | 16.7 | X | — |
| Hydroxypropylcellulose-L | 15 | 10 | X | — |
| Hydroxypropylcellulose-L | 20 | 16.7 | X | — |
| Hydroxypropylcellulose-L | 16.7 | 16.7 | X | — |
| Hydroxypropylcellulose-L | 13.3 | 16.7 | X | — |
| Hydroxypropylcellulose-M | 5 | 16.7 | X | — |
| Hydroxypropylcellulose-M | 3 | 16.7 | X | — |
| Hydroxypropylcellulose-M | 1 | 16.7 | X | — |
| Hydroxypropylcellulose-H | 3 | 16.7 | X | — |
| Hydroxypropylcellulose-H | 2 | 16.7 | X | — |
| Hydroxypropylcellulose-H | 1 | 16.7 | X | — |
| Methylcellulose (SM-25) | 4 | 16.7 | X | — |
| Methylcellulose (SM-25) | 2 | 16.7 | X | — |
| Methylcellulose (SM-25) | 1 | 16.7 | X | — |
| Methylcellulose (SM-400) | 5 | 16.7 | X | — |
| Methylcellulose (SM-400) | 3 | 16.7 | X | — |
| Methylcellulose (SM-400) | 1 | 16.7 | X | — |
| Methylcellulose (SM-8000) | 3 | 16.7 | X | — |
| Methylcellulose (SM-8000) | 2 | 16.7 | X | — |
| Methylcellulose (SM-8000) | 1 | 16.7 | X | — |
| Dextran (MW40000) | 50 | 11.4 | ○ (15000 rpm × 2 min) | — |
| Dextran (MW70000) | 37.5 | 10 | ○ (15000 rpm × 2 min) | — |
| Hyaluronic acid (MW900000) | 3 | 16.7 | ○ (15000 rpm × 2 min) | — |
| Hyaluronic acid (MW900000) | 2 | 16.7 | ○ (15000 rpm × 2 min) | — |
| Hyaluronic acid (MW900000) | 1 | 16.7 | ○ (15000 rpm × 2 min) | — |
| Hyaluronic acid (MW900000) | 2.7 | 13.3 | ○ (15000 rpm × 2 min) | — |
| Partially neutralized polyacrylate (NP-600) | 3 | 16.7 | ○ (15000 rpm × 2 min) | Not measurable |
| Partially neutralized polyacrylate (NP-600) | 1.5 | 16.7 | ○ (15000 rpm × 2 min) | Not measurable |
| Partially neutralized polyacrylate (NP-800) | 3 | 16.7 | ○ (15000 rpm × ? min) | Not measurable |
| Partially neutralized polyacrylate (NP-800) | 1.5 | 16.7 | ○ (15000 rpm × ? min) | Not measurable |
| Hydroxypropyl methylcellulose (90SH-30000) | 3.75 | 10 | X | — |
| Hydroxypropyl methylcellulose (90SH-30000) | 2.5 | 20 | X | — |

TABLE 2-continued

| Polymer | Polymer concentration (%) | BSA concentration (%) | Compatibility | Coating content (μg) |
|---|---|---|---|---|
| Hydroxypropyl methylcellulose (65SH-1500) | 3.75 | 10 | X | — |
| Hydroxypropyl methylcellulose (65SH-1500) | 2.5 | 20 | X | — |
| Polyvinyl pyrrolidone (K29/32) | 35 | 20 | X | — |
| Polyvinyl pyrrolidone (K29/32) | 52.5 | 10 | X | — |
| Polyvinyl pyrrolidone (K90) | 15 | 20 | X | — |
| Polyvinyl pyrrolidone (K90) | 22.5 | 10 | X | — |
| Polyvinyl pyrrolidone (K90) | 10 | 13.3 | X | — |
| Polyvinyl pyrrolidone (K90) | 24 | 8 | X | — |
| Polyvinyl pyrrolidone (K90) | 10 | 26.7 | X | — |
| Polyvinyl pyrrolidone (K90) | 6 | 32 | X | — |
| Hydroxy methylcellulose (TC-5) | 15 | 5 | X | — |
| Hydroxy methylcellulose (TC-5) | 10 | 20 | X | — |
| Polyethylene glycol-20000 | 20 | 16.7 | X | — |
| Polyethylene glycol-20000 | 10 | 16.7 | X | — |
| Polyvinyl alcohol | 10 | 16.7 | X | — |
| Polyvinyl alcohol | 5 | 16.7 | X | — |
| Sodium Carboxymethyl Cellulose (CMC—Na) | 7.5 | 10 | X | — |
| Chondroitin sulfate A | 30 | 10 | X | — |

Tables 1 and 2 show the compatibility test results between OVA or BSA and each water soluble polymer as well as the BSA or OVA content to the microneedle by the coating. Pullulan, hydroxypropylcellulose (HPC), methylcellulose, hyaluronic acid and sodium polyacrylate exhibited high compatibility when the mixing ratio between a physiologically active substance and water soluble polymer is optimized. Pullulan in particular exhibited high compatibility even with a high concentration of OVA. Further, the microneedle was coated by the method shown in FIG. 4 using these solutions. As a result, pullulan had the highest value, followed by the order of hydroxypropylcellulose (SL), methylcellulose and hyaluronic acid. As for hydroxypropylcellulose (SL), the coating amount varied depending on the grade, and tended to decrease in the order of HPC-SL>HPC-L>HPC-H. The reason for this is presumably the tendency in which the viscoelasticity (viscosity) of the polymers increased as the molecular weight of hydroxypropylcellulose becomes lower, whereby the adherence to the microneedle is increased. In addition, methylcellulose had good compatibility with OVA, but no good conditions were observed with BSA. Hyaluronic acid had good compatibility with both OVA and BSA but had poor viscosity, failing to obtain a sufficient coating amount. Sodium polyacrylate had good compatibility but no adherence to the microneedle was found, being unsuitable as a coating carrier. The above results verify that the coating containing a substantially uniform high molecular physiologically active substance can be achieved by using the coating carrier compatible with a high molecular physiologically active substance.

The polymers used are as follows. Shin-Etsu Chemical methylcellulose (SM-25, SM-400, SM-8000), SHOWA DENKO polyacrylic acid (NP-600, NP-800), Shin-Etsu Chemical hydroxypropylmethylcellulose (90SH-30000, 65SH-1500, TC-5), and NIPPON SHOKUBAI polyvinyl pyrrolidone (K29/32, K90) were used.

Example 3

Drying Test of Polymer Aqueous Solutions

Figure 9:
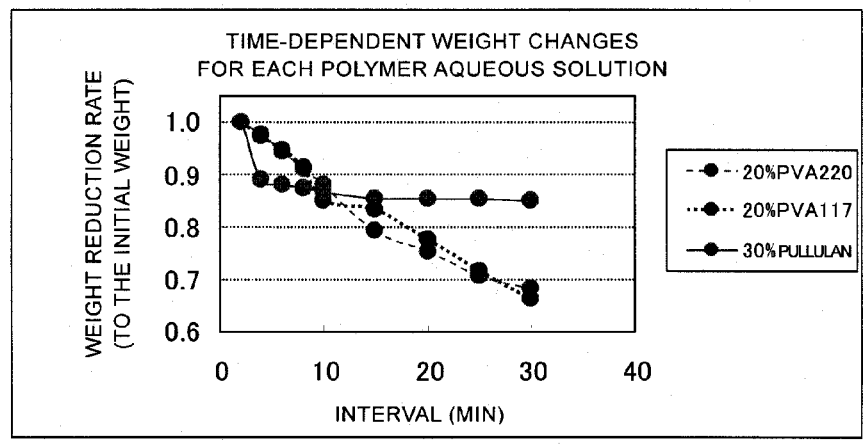
FIG. 9 is a graph showing an example of weight changes over time after spreading various polymer aqueous solutions.

Each coating solution of 20% PVA220, 20% PVA 117 and 30% pullulan was spread on a liner to give a thickness of 50 μm, and the liner was punched out to an area of 8 cm² and mounted on an electrobalance to measure time-dependent weight changes under a condition of room temperature. FIG. 9 is a graph showing an embodiment of time-dependent weight changes after spreading each polymer aqueous solution. In the graph, the horizontal axis shows the interval (min) and the longitudinal axis shows the weight reduction rate (to the initial weight). As shown in FIG. 9, two kinds of PVA exhibited a weight reduction tendency over time within the measurement time, while pullulan had substantially constant weight values despite the weight reduction at the initial stage and showed stable physical properties with the wettability maintained.

Example 4

Relationship Between Pullulan Concentration and BSA Coating Amount

Figure 10:
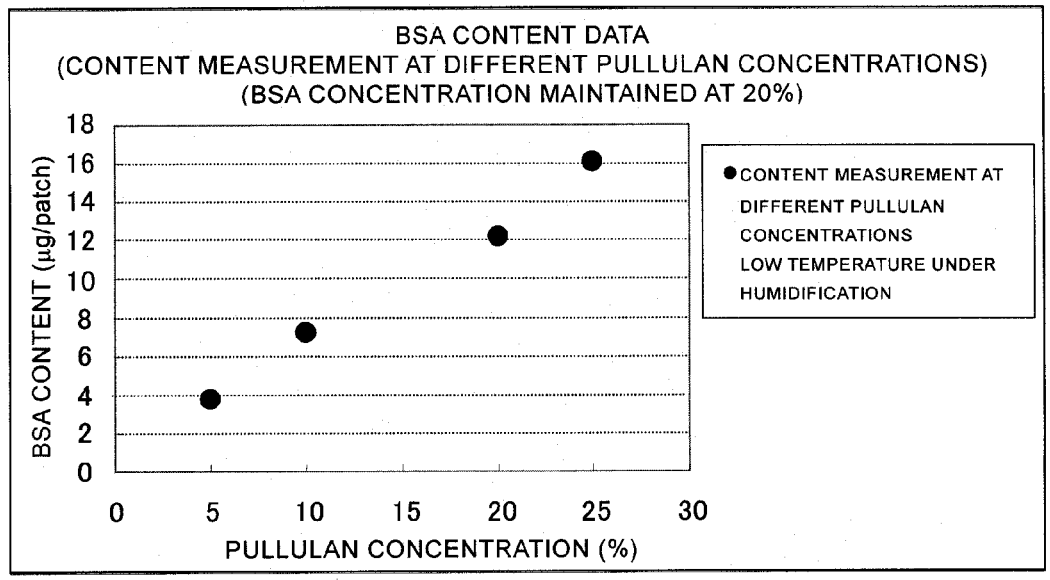
FIG. 10 is a graph showing an example of BSA content measurement results at different pullulan concentrations.

Determined Conditions
(a) Determined concentrations for the coating solution
  Pullulan concentrations: 5, 10, 20, 24 (%)
  BSA (model protein) concentration: 20 (%) fixed
(b) Microneedle
  Height 250 μm, 900 needles/cm², formulation area 1 cm²
(c) Metal mask plate
  Pitch: 300 μm, T (mask thickness): 100 μm, aperture: tetragonal configuration (200 μm per side)
(d) Conditions determined; room temperature and low temperature under humidification Operation Procedure As described above, the BSA (bovine serum albumin) concentration was maintained at 20% to prepare coating solutions having four determined pullulan concentrations. The coating was carried out by the method shown in FIG. 4 described earlier. Under a humidification condition, the coating solution was filled to the metal mask apertures using a spatula. The microneedle (needle) was inserted in the apertures filled with the solution, and the coated microneedle was then extracted with 1 mL of purified water to measure the BSA content (amount adhered) by BCA method (BSA standard). Table 3 and FIG. 10 show the results. In FIG. 10, the horizontal axis shows the pullulan concentration (%) and the longitudinal axis shows the BSA content (μg/patch).

TABLE 3

| Pullulan concentration (%) | BSA content (μg/patch) | Coefficient of variation (CV) (n = 10) | Viscosity (cps) |
|---|---|---|---|
| 5 | 3.7 | 56.1 | 200 |
| 10 | 7.2 | 41.2 | 400 |
| 20 | 12.2 | 25.2 | 2000 |
| 25 | 16.1 | 30.5 | 10000 |

As shown in Table 3, the solution viscosity is increased as the pullulan concentration is increased, and the BSA content is also increased depending on the viscosity increase. When the solution has a high viscosity (2000 cps, 10000 cps), the BSA coating amounts are greater compared with those having a low viscosity (200 cps, 400 cps), exhibiting the tendency in which the coefficient of variation (CV %) decreases. Accordingly, the viscosity of coating solution is preferably 500 cps or higher in view of securement and precision of the drug to be coated.

Example 5

Relationship Between the Viscosity and BSA Concentration in Pullulan

Figure 11:
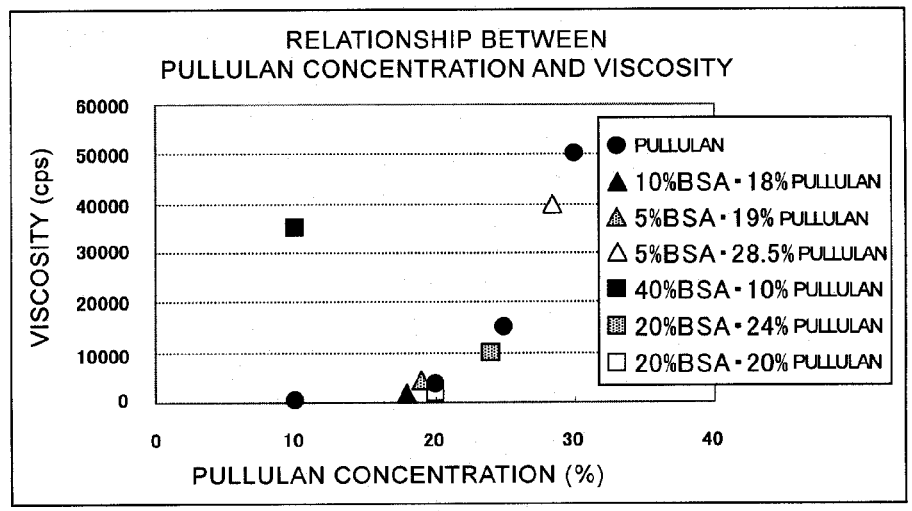
FIG. 11 is a graph showing an example of the correlation between pullulan concentration and viscosity.

Determined Conditions
(a) Determined concentration in pullulan aqueous solution: 5 to 30 (%)
(b) Determined concentration in pullulan base coating solution
Pullulan: 10 to 28.5 (%)
BSA=5 to 40 (%)
Operation Procedure The viscosity of aqueous solutions prepared to meet the above conditions was measured using a viscometer (RION viscotester VF-04). The results are shown in FIG. 11 as the relationship between the pullulan concentration and the viscosity. As shown in FIG. 11, the aqueous solutions containing pullulan singly had viscosity increases in a quadratic-curve manner as the pullulan concentration increased. In the combination of pullulan and BSA, the viscosity properties depending on the pullulan concentration were found when the BSA concentration is set to low values, whereas the viscosities were found deviated from the above pullulan concentration dependency when the BSA concentration was under a dominant solution condition (40% BSA, 10% pullulan). The results shown in FIG. 11 reveal that when a high molecular physiologically active substance has a low solubility to a solvent, or the like, and the concentration thereof is determined to be a low value for designing a formulation, the viscosity of coating solution can be controlled by suitably setting the concentration of coating carrier (pullulan, etc.), thereby attaining an intended coating amount.

Industrial Applicability

According to the present invention, the quantitative coating of a physiologically active substance to the microneedles is not only enabled, but a microneedle device provided with microneedles coated using a screen printer can also be mass-produced. Thus, the convenience of the microneedle is remarkably enhanced whereby the microneedle is industrially applicable.

The invention claimed is:

1. A method of coating microneedles comprising the steps of:
filling a coating solution on a flat mask plate having blind holes as apertures arranged in rows and columns into the apertures using a spatula as a filling means so that the apertures are filled to capacity with the coating solution, and inserting microneedles of a microneedle device to the apertures filled with the coating solution to coat the microneedles.

2. The method of coating microneedles according to claim 1, wherein the steps are carried out at a relative humidity of 70.0 to 100% RH.

3. The method of coating microneedles according to claim 1, wherein the coating solution contains a carrier having a molecular weight of 1000 or more compatible with a physiologically active substance having a molecular weight of 1000 or more.

4. The method of coating microneedles according to claim 3, wherein the carrier having a molecular weight of 1000 or more is a polysaccharide.

5. The method of coating microneedles according to claim 4, wherein the polysaccharide is one or more selected from the group consisting of pullulan, hydroxypropylcellulose and hyaluronic acid.

6. The method of coating microneedles according to claim 1, wherein a coating amount to the microneedle is adjusted by changing at least one of
a. an opening diameter of the apertures formed on the mask plate,
b. a viscosity of the coating solution,
c. a clearance between the mask plate and the microneedle basal surface,
d. a spatula pressure,
e. a speed of spatula stroke,
f. a thickness of the mask plate, and
g. an attack angle between the spatula and the mask plate.

7. The method of coating microneedles according to claim 6, wherein an opening diameter of the apertures formed on the mask plate is in a range of 100 μm$^2$ to 90000 μm$^2$, which exceeds a cross sectional area of the microneedle at a lower end of the apertures when inserting the microneedle.

8. The method of coating microneedles according to claim 6, wherein a viscosity of the coating solution is in a range of 500 cps to 60000 cps.

9. The method of coating microneedles according to claim 6, wherein a clearance between the mask plate and the microneedle basal surface is in a range of 0 to 500 μm.

10. The method of coating microneedles according to claim 6, wherein a spatula pressure is in a range of 0.001 to 0.4 MPa.

11. The method of coating microneedles according to claim 6, wherein a thickness of the mask plate is in a range of 10 to 500 μm.

12. The method of coating microneedles according to claim 6, wherein an attack angle between the spatula and the mask plate is in a range of 65° to 90°.

13. The method of coating microneedles according to claim 6, wherein a speed of spatula stroke is in a range of 2 to 800 mm/sec.

14. A microneedle device comprising microneedles coated by the coating method of claim 1.

* * * * *